United States Patent [19]
Strong

[11] Patent Number: 5,625,068
[45] Date of Patent: Apr. 29, 1997

[54] SUBSTITUTED QUINOLINE HERBICIDE INTERMEDIATES AND PROCESS

[75] Inventor: Henry L. Strong, Somerset, N.J.

[73] Assignee: American Cyanamid Company, Madison, N.J.

[21] Appl. No.: 464,192

[22] Filed: Jun. 5, 1995

[51] Int. Cl.$^6$ .................... C07D 215/18; C07D 215/40
[52] U.S. Cl. ................................ 546/171; 546/180
[58] Field of Search .................... 546/171, 180

[56] References Cited

U.S. PATENT DOCUMENTS

| | | | |
|---|---|---|---|
| 3,252,858 | 5/1966 | Goodhue | 167/46 |
| 4,888,427 | 12/1989 | Bodor | 546/316 |
| 5,281,713 | 1/1994 | Strong et al. | 546/179 |
| 5,334,576 | 8/1994 | Doehner, Jr. et al. | 504/128 |

FOREIGN PATENT DOCUMENTS 0284174  9/1988  European Pat. Off. .

Primary Examiner—C. Warren Ivy
Assistant Examiner—Evelyn Huang
Attorney, Agent, or Firm—Joseph M. Mazzarese

[57] ABSTRACT

The invention is herbicide 3-substituted quinoline intermediates and a method for the synthesis of the herbicide intermediates 3-alkoxymethyl substituted quinolines.

17 Claims, No Drawings

SUBSTITUTED QUINOLINE HERBICIDE INTERMEDIATES AND PROCESS

SUMMARY OF THE INVENTION

The invention is substituted quinoline intermediates useful in the synthesis of the herbicide 2-(4-isopropyl-4-methyl-5-oxo-2-imidazolidinyl)-5-methoxymethylnicotinic acid and a process for preparing herbicide intermediates 3-alkoxymethyl substituted quinolines.

DETAILED DESCRIPTION

The invention is compounds of the formula

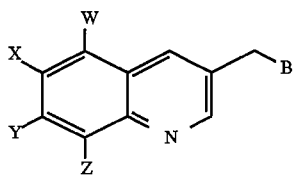

wherein W, X, Y and Z are independently H, halogen, $NO_2$, $NH_2$ or —O—alkyl straight or branched $C_1$-$C_6$; and B is chlorine, bromine or a quaternary ammonium halide or B may be —O—alkyl straight or branched $C_1$-$C_6$ provided that W, X and Y are not H and Z is not OH or —O—alkyl; and Z may be OH provided that W, X and Y are not H and B is not —O—alkyl; and a process for preparing compounds of the formula

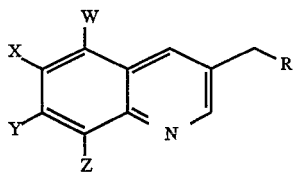

wherein W, X, Y and Z are independently H, halogen, $NO_2$, $NH_2$, OH or —O—alkyl straight or branched $C_1$-$C_6$ and R is —O—alkyl straight or branched $C_1$-$C_6$ which comprises reacting a compound of the formula

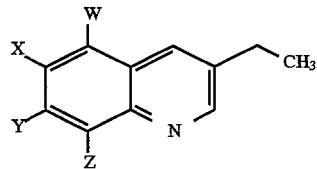

wherein W, X, Y and Z are independently H, halogen, $NO_2$ or —O—alkyl straight or branched $C_1$-$C_6$ with a radical halogenating reagent wherein halogen is bromine or chlorine to form a compound of the formula

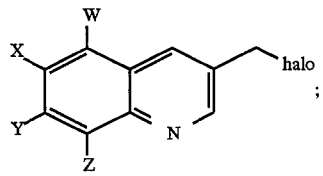

reacting compound III with a tertiary amine to form a compound of the formula

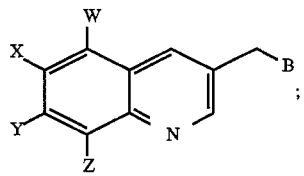

and reacting compound IV with RM, a metal alkoxide, wherein R is —O—alkyl straight or branched $C_1$-$C_6$ and M is Na, Li or K to form the 3-alkoxymethyl substituted quinoline compounds of the formula I.

The 3-alkoxymethyl substituted quinolines of the invention are herbicide intermediates useful in the synthesis of the substituted quinoline herbicide intermediates to the herbicide intermediate 5-methoxymethyl-2,3-pyridinedicarboxylic acid for the herbicide 2-(4-isopropyl-4-methyl-5-oxo- 2-imidazolidinyl)-5-methoxymethylnicotinic acid of U.S. Pat. No. 5,334,576.

The invention is further illustrated in the examples, below, but is not to be deemed limited thereby.

EXAMPLE 1

Preparation of 3-(Bromomethyl)-8-nitroquinoline

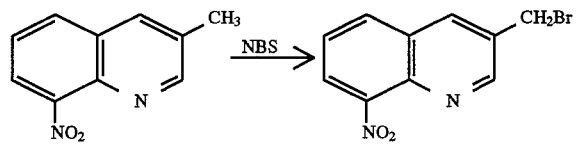

A stirred mixture of 3-methyl-8-nitroquinoline (9.5 g, 0.05 mol) in chlorobenzene (75 mL) is heated to 80° C. under nitrogen. A mixture of N-bromosuccinimide (9.0 g 0.05 mol), and 2,2'-azobisisobutyronitrile (0.5 g, 0.003 mol) is added to the reaction mixture. The reaction mixture is held at 80°–90° C. for 1 hour. The mixture is washed with water (100 mL) at 60°–80° C., cooled to room temperature and filtered to obtained a solid. The solid is washed with chlorobenzene and vacuum dried to give the title product as light-yellow solid (3.9 g mp 121°–124° C.) which is identified by $^1H$ and 13C NMR spectral analyses.

EXAMPLE 2

Preparation of (8-Nitro-3-quinolyl) methyltrimethylammonium bromide

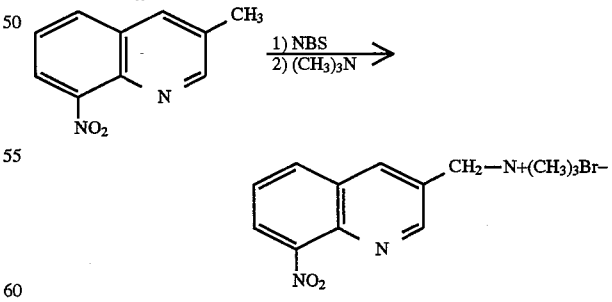

A stirred mixture of 3-methyl-8-nitroquinoline (75 g, 0.40 mol) in chlorobenzene (1000 mL) is heated to 80° C. under nitrogen. A mixture of N-bromosuccinimide (75 g 0.42 mol), and 2,2'-azobisisobutyronitrile (4 g, 0,024 mol) is added to the reaction mixture over 30 minutes at 80°–90° C. After the addition is complete, the reaction mixture is held a 80°–90°

C. for 4 hours. The mixture is washed with water (400 mL) at 60°–80° C. and the organic mixture is diluted with acetone (300 mL). The mixture is cooled to 10° C. and anhydrous trimethylamine (49 g, 0.83 mol) is added. The mixture is stirred overnight at 10°–30° C. and filtered to obtained a solid. The solid is washed with acetone and vacuum dried to give the title product as light-yellow solid (74.0 g) which is identified by 1H and 13C NMR spectral analyses.

EXAMPLE 3

Preparation of 3-(Methoxymethyl)-8-nitroquinoline

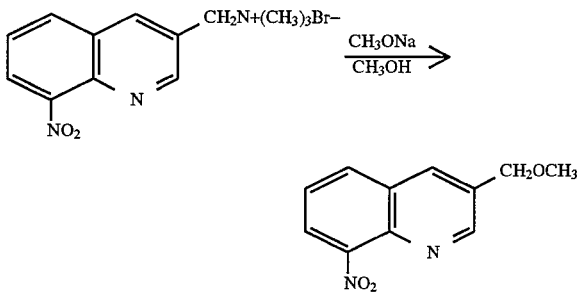

A mixture of 25% sodium methoxide(88 g, 0.19 mol) in methanol (600 mL) and (8-nitro-3-quinolyl) methyltrimethylammonium bromide(63 g, 0.19 mol) is heated under nitrogen at reflux for 2 hours and cooled to room temperature. The resulting mixture is diluted with ice water (600 mL) and filtered to obtained a solid. The solid is washed with water and vacuum dried to give the title product as an off-white solid (32.2 g, mp 69°–71° C.) which is identified by $^1$H and $^{13}$C NMR spectral analyses.

EXAMPLE 4

Preparation of 3-(Methoxymethyl)-8-aminoquinoline

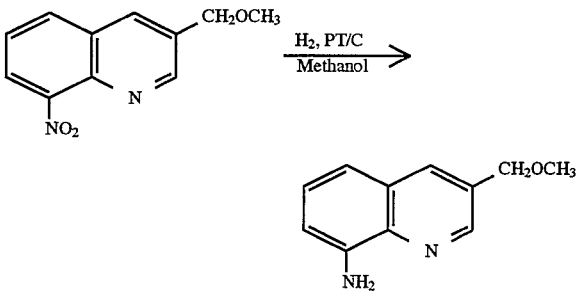

A mixture of 3-(methoxymethyl)-8-nitroquinoline (5.64 g 0.026 mol), 5% palladium on carbon (0.32 g) and methanol (70 mL) in a pressure vessel is heated to 45° C. The mixture is treated with hydrogen at 30 psig for 4 hours at 45° C. and cooled to room temperature. The mixture is filtered to remove the palladium on carbon and the cake is washed with methanol. The combined filtrate and wash is concentrated in vacuo to obtain the title product as a clear liquid (4.7 g) which is identified by $^1$H and $^{13}$C NMR spectral analyses.

EXAMPLE 5

Preparation of 3-(Bromomethyl)-8-chloroquinoline

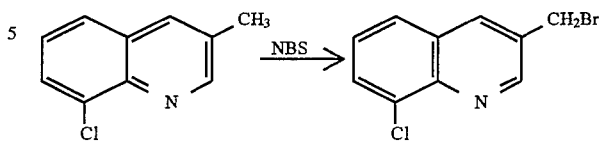

A stirred mixture of 3-methyl-8-chloroquinoline (9 g, 05 mol) in chlorobenzene (75 mL) is heated to 80° C. under nitrogen. A mixture of N-bromosuccinimide (9.0 g 0.05 mol). and 2,2,-azobisisobutyronitrile (0.5 g, 0.003 mol) is added to the reaction mixture. The reaction mixture is held a 80°–90° C. for 1 hour. The mixture is washed twice with water (50 mL) at 60°–80° C. and cooled to room temperature. The mixture is diluted with heptane (75 mL) and filtered to obtained a solid which is washed with chlorobenzene and then with heptane. The solid is vacuum dried to give the title product as an off-white solid (6.2 g, mp 125°–129° C.) which is identified by $^1$H and $^{13}$C NMR spectral analyses.

EXAMPLE 6

Preparation of (8-Chloro-3-quinolyl)methyltrimethylammonium bromide

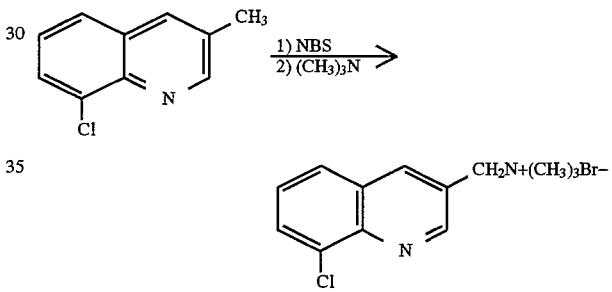

A stirred mixture of 3-methyl-8-chloroquinoline (71.2 g, 0.4 mol) in chlorobenzene (700 mL) is heated to 80° C. under nitrogen. A mixture of N-bromosuccinimide (71.2 g, 0.4 mol). and 2,2'-azobisisobutyronitrile (4 g, 0,024 mol) is added to the reaction mixture over 30 minutes at 80°–90° C. After the addition is complete, the reaction mixture is held a 80°–90° C. for 1.5 hours. The mixture is washed twice with water (300 mL) at 60°–80° C. and the organic mixture is diluted with acetone (250 mL). The mixture is cooled to 10° C. and anhydrous trimethylamine (29.5 g, 0.5 mol) is added. The mixture is stirred at 10°–30° C. for 3 hours and filtered to obtained a solid. The solid is washed with acetone and vacuum dried to give the title product as an off-white solid (69.4 g) which is identified by $^1$H and $^{13}$C NMR spectral analyses.

EXAMPLE 7

Preparation of 3-(Methoxymethyl)-8-chloroquinoline

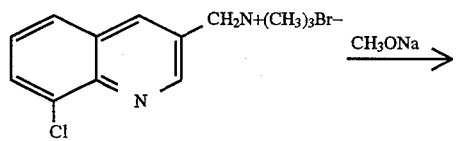

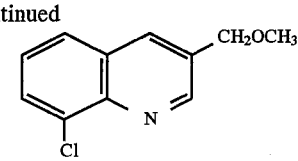

A mixture of 25% sodium methoxide(66 g, 0.3 mol) in methanol (600 mL) and (8-chloro-3-quinolyl) methyltrimethylammonium bromide (66 g, 0.21 mol) is heated under nitrogen at reflux for 3 hours and cooled to room temperature. The resulting mixture is diluted with ice water (500 mL) and extracted twice with methylene chloride (200 mL). The extracts are combined, washed with water, and concentrated in vacuo to obtain the title product as a clear liquid (39.4 g) which is identified by $^1$H and $^{13}$C NMR spectral analyses.

EXAMPLE 8

Preparation of 3-(Methoxymethyl)-5-nitro-8-chloroquinoline

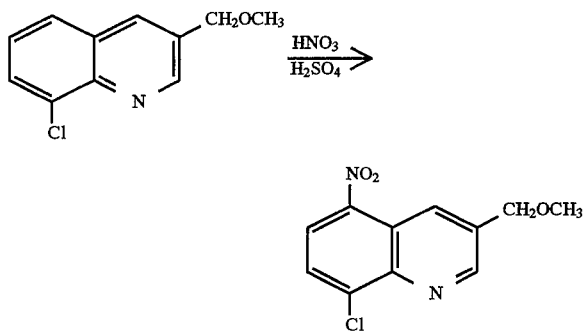

3-(Methoxymethyl)-8-chloroquinoline (10.3 g, 0.05 mol) is added to 96% sulfuric acid (40 g, 0.39 mol) at 10°–30° C. and 70% nitric acid is then added over 15 minutes. The reaction mixture is stirred at room temperature for 14 hours, diluted with ice water (150 mL) and filtered to obtain a solid. The solid is washed with water and vacuum dried to give the title product as a yellow solid (9.4 g, mp 83°–86° C.) which is identified by 1H and $^{13}$C NMR spectral analyses.

EXAMPLE 9

Preparation of (7,8-Dichloro-3-quinolyl) methyltrimethylammonium bromide

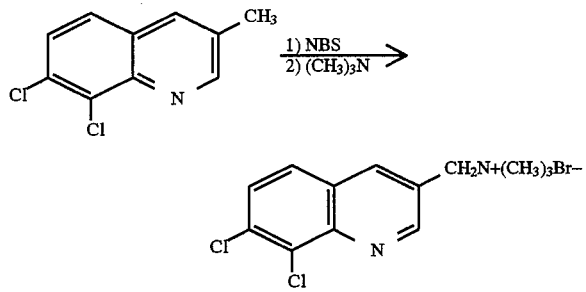

A stirred mixture of 3-methyl-7,8-dichloroquinoline (106 g, 0.5 mol) in chlorobenzene (1000 mL) is heated to 80° C. under nitrogen. A mixture of N-bromosuccinimide (89 g 0.5 mol). and 2,2'-azobisisobutyronitrile (3 g, 0.02 mol) is added to the reaction mixture over 30 minutes at 80°–90° C. After the addition is complete, the reaction mixture is held a 80°–90° C. for 2 hours. The mixture is washed with water (400 mL) at 60°–80° C. and the organic mixture is diluted with acetone (300 mL). The mixture is cooled to 10° C. and anhydrous trimethylamine (49 g, 0.83 mol) is added. The mixture is stirred overnight at 10°–30° C. and filtered to obtained a solid. The solid is washed with acetone and vacuum dried to give the title product as a white solid (129 g) which is identified by $^1$H and $^{13}$C NMR spectral analyses.

EXAMPLE 10

Preparation of 3-(Methoxymethyl)-7,8-dichloroquinoline

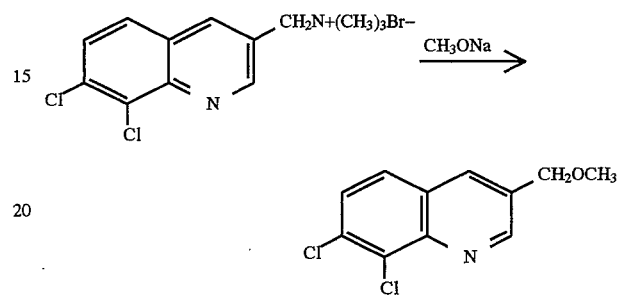

A mixture of 25% sodium methoxide(100 g, 0.46 mol) in methanol (800 mL) and (7,8-dichloro-3-quinolyl) methyltrimethylammonium bromide(110 g, 0.31 mol) is heated under nitrogen at reflux for 2 hours and cooled to room temperature. The resulting mixture is diluted with ice water (800 mL) and filtered to obtained a solid. The solid is washed with water and vacuum dried to give the title product as an off-white solid (64.30 g,) which is identified by $^1$H and $^{13}$C NMR spectral analyses.

EXAMPLE 11

Preparation of (5,8-Dichloro-3-quinolyl) methyltrimethylammonium bromide

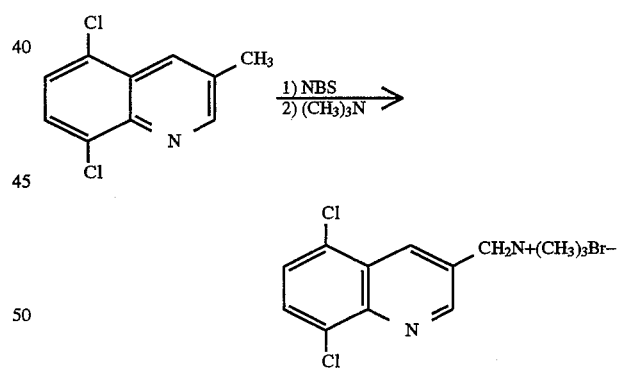

A stirred mixture of 3-methyl-5,8-dichloroquinoline (143 g, 0.67 mol) in chlorobenzene (1000 mL) is heated to 80° C. under nitrogen. A mixture of N-bromosuccinimide (120 g 0.67 mol). and 2,2'-azobisisobutyronitrile (5 g, 0.03 mol) is added to the reaction mixture over 30 minutes at 80°–90° C. After the addition is complete, the reaction mixture is held a 80°–90° C. for 3 hours. The mixture is washed with water (600 mL) at 60°–80° C. and the organic mixture is diluted with acetone (200 mL). The mixture is cooled to 10° C. and anhydrous trimethylamine (65 g, 1.1 mol) is added. The mixture is stirred overnight at 10°–30° C. and filtered to obtained a solid. The solid is washed with acetone and vacuum dried to give the title product as a white solid (174.6 g) which is identified by $^1$H and $^{13}$C NMR spectral analyses.

EXAMPLE 12

Preparation of 3-(Methoxymethyl)-5,8-dichloroquinoline

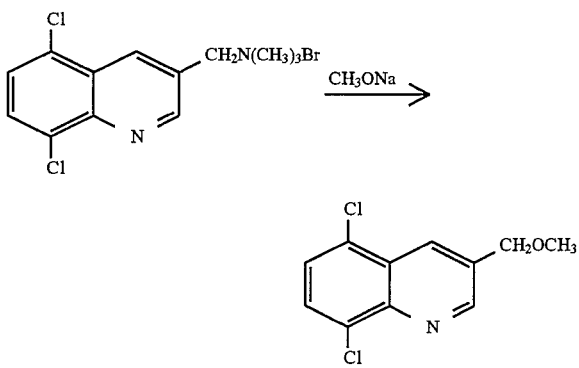

A mixture of 25% sodium methoxide(130 g, 0.6 mol) in methanol (800 mL) and (5,8-dichloro-3-quinolyl) methyltrimethylammonium bromide(146 g, 0.41 mol) is heated under nitrogen at reflux for 2 hours and cooled to room temperature. The resulting mixture is diluted with ice water (1200 mL) and filtered to obtained a solid. The solid is washed with water and vacuum dried to give the title product as a light-tan solid (91 g) which is identified by $^1$H and $^{13}$C NMR spectral analyses.

EXAMPLE 13

Preparation of (8-Chloro-3-quinolyl) methyltrimethylammonium bromide using 1,3-dibromo-5,5-dimethylhydantoin

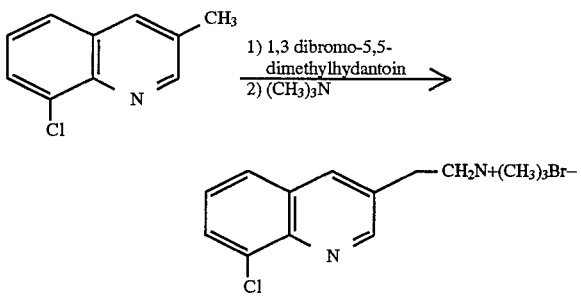

A stirred mixture of 3-methyl-8-chloroquinoline (71.2 g, 0.4 mol) in chlorobenzene (700 mL) is heated to 80° C. under nitrogen. A mixture of 1,3 dibromo-5,5-dimethylhydantoin (57 g, 0.02 mol), and 2,2'-azobisisobutyronitrile (4 g, 0.024 mol) is added to the reaction mixture over 30 minutes at 80°–90° C. After the addition is complete, the reaction mixture is held a 80°–90° C. for 1.5 hours. The mixture is washed twice with water (300 mL) at 60°–80° C. and the organic mixture is diluted with acetone (250 mL). The mixture is cooled to 10° C. and anhydrous trimethylamine (36 g, 0.6 mol) is added. The mixture is stirred at 10°–30° C. for 3 hours and filtered to obtained a solid. The solid is washed with acetone and vacuum dried to give the title product as off-white solid (34.1 g) which is identified by $^1$H and $^{13}$C.

What is claimed is:

1. A compound of the formula

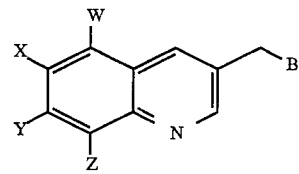

wherein W, X, and Y are independently H, halogen, NO$_2$, NH$_2$ or —O—alkyl straight or branched C$_1$–C$_6$, Z is H, OH, halogen, NO$_2$, NH$_2$ or —O—alkyl straight or branched C$_1$–C$_6$ and B is a quaternary ammonium halide or —O—alkyl straight or branched C$_1$–C$_6$, provided that when B is —O—alkyl either W, X and Y are not H or Z is not OH or —O—alkyl [; or Z is OH provided that W, X and Y are not H and B is not —O—alkyl].

2. A compound according to claim 1 wherein W, X and Y are each H, and Z is chlorine.

3. A compound according to claim 1 wherein W, X and Y are each H, Z is chlorine and B is a trimethyl ammonium bromide.

4. A compound according to claim 1 wherein W, X and Y are each H, Z is chlorine and B is methoxy.

5. A compound according to claim 1 wherein W, X and Y are each H, and Z is NO$_2$.

6. A compound according to claim 1 wherein W, X and Y are each H, Z is NO$_2$ and B is trimethyl ammonium bromide.

7. A compound according to claim 1 wherein W, X and Y are each H, Z is NO$_2$ and B is methoxy.

8. A compound according to claim 1 wherein W, X and Y are each H, Z is NH$_2$ and B is methoxy.

9. A compound according to claim 1 wherein X and Y are H, W is NO$_2$, Z is chlorine and B is —O—CH$_3$.

10. A compound according to claim 1 wherein X and W are H, Y and Z are chlorine and B is trimethylammonium bromide.

11. A compound according to claim 1 wherein X and W are H, Y and Z are chlorine and B is —OCH$_3$.

12. A compound according to claim 1 wherein X and Y are H, W and Z are chlorine and B is —OCH$_3$.

13. A compound according to claim 1 wherein X and Y are H, W and Z are chlorine and B is trimethylammonium bromide.

14. A process for preparing a compound of the formula

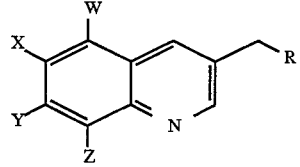

wherein W, X, Y and Z are independently H, halogen, or NO$_2$, and R is —O—alkyl straight or branched C$_1$–C$_6$ which comprises reacting a compound of the formula

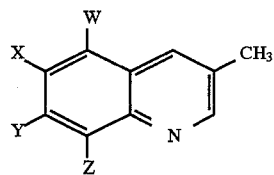

wherein W, X, Y and Z are independently H, halogen, or $NO_2$ with a radical halogenating reagent wherein the halogen is bromine or chlorine to form a compound of the formula

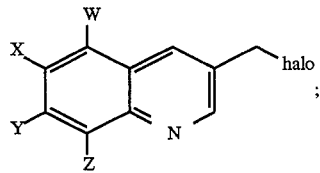

reacting compound III with a tertiary amine to form a compound of the formula

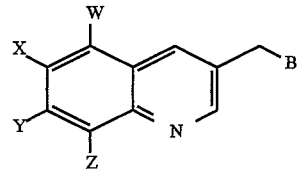

wherein B is a tertiary ammonium halide; and reacting compound IV with RM wherein R is —O—alkyl straight or branched C1–C6 and M is Na, Li or K to form the compound of formula I.

15. A process according to claim 14 wherein RM is sodium methoxide.

16. A process according to claim 14 wherein the radical halogenating agent to form compound III is N-bromosuccinimide and the tertiary amine to form compound IV is trimethyl amine.

17. A process according to claim 14 wherein the radical halogenating agent to form compound III is 1,3-dibromo-5,5-dimethylhydantoin and the tertiary amine is trimethylamine.

* * * * *

UNITED STATES PATENT AND TRADEMARK OFFICE
CERTIFICATE OF CORRECTION

PATENT NO.   : 5,625,068
DATED        : April 29, 1997
INVENTOR(S)  :
              Henry L. Strong It is certified that error appears in the above-indentified patent and that said Letters Patent is hereby corrected as shown below:

In column 8, lines 19-20, delete the bracketed term.

Signed and Sealed this

Ninth Day of September, 1997

Attest:

BRUCE LEHMAN

Attesting Officer

Commissioner of Patents and Trademarks